United States Patent [19]

Lewenstein

[11] Patent Number: 4,774,226

[45] Date of Patent: Sep. 27, 1988

[54] PHARMACEUTICAL PREPARATION FOR THE PROPHYLACTIC TREATMENT OF ALLERGIES AND PROCESS FOR THE PREPARATION OF SAID PHARMACEUTICAL PREPARATION

[75] Inventor: Ari Lewenstein, Lugano, Switzerland

[73] Assignee: Cernitin S.A., Barbengo, Switzerland

[21] Appl. No.: 860,127

[22] Filed: May 6, 1986

[30] Foreign Application Priority Data

May 6, 1985 [CH] Switzerland ............... 1918/85

[51] Int. Cl.⁴ ............................................ A61K 37/02
[52] U.S. Cl. ........................................ 514/8; 514/2; 514/826
[58] Field of Search ............... 424/195.1; 435/931; 514/867, 882, 925, 8, 2, 826

[56] References Cited

U.S. PATENT DOCUMENTS 3,360,437 12/1967 Carlsson ........................ 435/931

Primary Examiner—Delbert K. Phillips
Attorney, Agent, or Firm—Shenier & O'Connor

[57] ABSTRACT

A pharmaceutical preparation for the prophylactic treatment of allergies which contains as active ingredient an extract of pollen which contains nor more than 5% by weight, referred to the dry weight of the extract of pollen, of proteins having a high molecular weight or which is completely free of proteins of high molecular weight. The active ingredients of the inventive pharmaceutical preparation have themselves no allergen activity. To those human beings and children which in the years before suffered from severe symptoms of hay fever or asthma, the inventive pharmaceutical preparations were administered, preferably orally, during about three months before the allergy usually had occurred, for instance in the months February until April. By said administration the occurring of the pollen allergy in spring time and during the whole summer could be completely prevented. The inventive pharmaceutical preparations are prepared by extracting the pollen of plants with an aqueous extraction medium, and by metabolizing high molecular proteins of the pollen with a microorganism yielding low molecular proteins or amino acids. Thereafter the aqueous extraction medium is separated from the pollen and the pollen are extracted further with a not aqueous extraction medium. The concentrated extract or the dry residue of the extract recovered with the aqueous medium or the not aqueous medium or a mixture of the extracts or dry residues recovered with the aqueous medium and the not aqueous medium are the active ingredient of the inventive pharmaceutical preparations.

24 Claims, No Drawings

PHARMACEUTICAL PREPARATION FOR THE PROPHYLACTIC TREATMENT OF ALLERGIES AND PROCESS FOR THE PREPARATION OF SAID PHARMACEUTICAL PREPARATION

BACKGROUND OF THE INVENTION

Prophylactic therapeutical treatment for preventing allergies like hay-feaver or allergic asthma well known in the art. Said treatments, however, are troublesome and time consuming because the administration by injection of increasing dosages of the allergen, for example pollen of plants or of special fractions of human gammaglobulin is required.

The aim of the present invention was to provide a new pharmaceutical preparation for the prophylactic treatment of allergies which pharmaceutical preparation can be administered orally or eventually also topically.

DESCRIPTION OF THE PRIOR ART

According to a well known procedure for the prophylactic treatment of allergies like hay-fever or allergic asthma there are first performed tests on the skin of the person to be submitted to such a treatment with substances which are usual allergens, like for instance pollen of plants, hairs of mammals or feathers of birds, in order to find out by which allergen the allergic response of the organism of the person to be treated is caused. Thereafter a desensibilizing treatment is performed in which increasing dosages of the allergen which provokes the allergic reaction like e.g. pollen of plants, are administered to the person by injections. Said desensibilizing treatment is not only time consuming, troublesome and expensive but it is also rather risky for the person to be treated, specially because the pharmaceutical preparations used for performing said desensibilizing treatment are often not sufficiently pure. Furthermore, if the person which is submitted to such a prophylactic treatment is unexpectedly contacted with the allergen in question during said treatment then a very severe irritation or inflammation can occur, and in extreme situations even an anaphylactic shock can be evoked.

In recent times it was tried to avoid said risk of the above stated prophylactic desensibilizating treatment by performing a prophylactic general desensibilization of the person to be treated by administering by injection special fractions of human gammaglobulin. According to said prophylactic treatment no preceding skin tests are performed in order to find out which substances actually evoke the allergic reaction of the person to be treated but about three months before the start of the allergy in question is to be expected the fraction of human gammaglobulin is administered by injection. The treatment does not bring about the above mentioned risks of the specific desensibilization treatment, however also said more recent prophylactic treatment is very time consuming, troublesome and expensive because usually 9 or more administrations by injections have to be made over a period of several weeks. Furthermore, it is impossible to predict the dosage which is necessary in order to achieve the prevention of the allergy and if the injected dosages were too low, the allergy occurs in the usual severeness when the person in question is contacted with the allergen in question.

It is known that pollen contains a multitude of substances valuable as nutrients and therefore many dietethic products or cosmetic products containing pollen of plants are available in the market. Because of the high molecular proteins present in the hull of the pollen, however, preparations which contain pollen of plants can evoke an allergic reaction if the person who uses the corresponding product is sensitive to the allergen in question.

In the U.S. Pat. No. 3,360,437 of C. G. Carlsson et al. there is described a process according to which the important constituents from pollen are recovered, avoiding in the products in question the high molecular protein constituents of the pollen which may cause allergies. According to said process the important constituents from pollen are obtained by an extraction which comprises:

(a) extracting pollen with an aqueous solution of a member selected from the group consisting of ethylm alcohol and acetone, (b) subjecting the resulting extract in the presence of the pollen to digestion with Mucor hiemalis for a period of about 48 hours, (c) separating the resulting digested solution from the pollen residue, According to a further process described in said U.S. patent the important constituents from pollen are recovered by an extraction which comprises:

(a) extracting pollen with an aqueous solution of a member selected from the group consisting of ethyl alcohol and acetone, (b) subjecting the resulting extract in the presence of the pollen to digestion with Mucor hiemalis for a period of about 48 hours, (c) separating the resulting digested solution from the pollen residue, (d) subjecting the pollen residue to extraction with a volatile lipid-solving solvent selected from the group consisting of ethyl ether and acetone, and (e) separating the resulting extract from the pollen residue.

Also a combined extraction of the pollen with an aqueous solution of ethyl alcohol and acetone and a further extraction with a volatile lipid-solving solvent selected from the group consisting of ethyl ether and acetone is described in said U.S. patent.

The digestion of the high molecular proteins of the pollen with the mold of the genus Mucor performed according to said process results in that the so produced products are free of substances which may cause allergies if persons which are sensitive to said high molecular proteins consume the products in question (see e.g. column 1, lines 60–65, and column 2, lines 58–64 of said U.S. patent).

Similar processes as the process described in the above stated U.S. patent, according to which several further strains of Mucor are used in order to perform the digestion of the pollen are described in the Austrian Pat. No. 255 643 and the German Pat. No. 1,467,750.

The extracts of pollen prepared according to said prior art processes using an aqueous extraction medium or a not aqueous extraction medium or mixtures of the extracts recovered with the aqueous extraction medium and the not aqueous extraction medium are available in the market. Said products are used as tonics, restorative products, for the treatment of prostatic diseases, for accelerating the healing of wounds and fractures and as antiinflammatory products. Said products can be administered orally or topically, for example as ointments or similar products for healing wounds.

As already stated above before said products were brought onto the market tests were performed in order to show that the products containing the extracts of pollen which are essentially free of high molecular proteins do not cause allergies.

It was now quite unexpectedly found out that said prior art products available in the market and similar products which contain as active ingredient an extract of pollen can be used for a prophylactic treatment of allergies.

SUMMARY OF THE INVENTION

The present invention, accordingly, concerns pharmaceutical preparations for the prophylactic treatment of allergies which contain as active ingredient extracts of pollen which are essentially free of proteins having a high molecular weight.

The present invention furthermore concerns processes for the preparation of said pharmaceutical preparations.

DETAILED DESCRIPTION OF THE INVENTION

One object of the present invention, accordingly, is a pharmaceutical preparation for the prophylactic treatment of allergies which contains as active ingredient an extract of pollen which contains not more than 5% by weight, referred to the dry weight of the extract of pollen, of proteins having a high molecular weight or which is completely free of proteins having a high molecular weight.

Preferably the inventive pharmaceutical preparations are preparations for the oral administration. Such inventive pharmaceutical preparations, however, can be also formulated so that they are suitable for a topic administration, for example as solutions or ointments to be administered into the nose or the eye, as sprayable compositions packed in a non corrosive pressure resistant container equipped with a spraying nozzle, which sprays can be administered to prevent hay fever or allergic asthmatic diseases, or as oinments or similar formulations to be applied onto the skin. If desired, the preparations can be also formulated so that they can be administered by injection.

In the inventive pharmaceutical preparations the extract of pollen is preferably an extract of pollen of plants of the plant family of the conifers, or plants of the plant family of the cereals and grasses, i.e. the gramineae. Of the pollen of the plants of the family of the conifers those of the subfamily pinaceae is specially preferred. From the plant family of the cereals and grasses those of the subfamily framineae are preferred, and preferred types of pollen of said class are those of corn having the Latin name Zea mays, from rye having the Latin name Secale cereale and of the grass having the Latin name Phleum pratense.

It is specially preferred to use in the inventive pharmaceutical product a mixture of extracts which were recovered from pollen of the plant family of conifers and/or pollen which were recovered from the plant family of cereals and/or grasses together with pollen of plants of other plant families than the above stated type, like e.g. pollen of the plant family of the liliacea, the compositae, the rosaceae, the salicaceae, the betulaceae or the ulmaceae.

The extract of pollen contained in the inventive pharmaceutical preparations can be an extract which was recovered by an extraction performed with an aqueous extraction medium or a not aqueous extraction medium or the extract of pollen can be a mixture of an extract recovered using an aqueous extraction medium and an extract recovered using a not aqueous extraction medium.

A further object of the present invention is a process for the preparation of the inventive pharmaceutical preparation in which process freshly harvested or dry pollen of plants are extracted with an aqueous extraction medium and thereafter the high molecular proteins present in said aqueous extract are metabolized by microorganisms yielding proteins of low molecular weight and/or amino acids and wherein said proteins of high molecular weight are metabolized until a content of the extract of said proteins of not more than 5% by weight, referred to the dry weight of the extract of pollen is reached or until the extract is completely free of proteins having a high molecular weight and wherein the pollen are recovered from the aqueous medium and said residue of pollen is further extracted with a not aqueous medium and said second extract is as well recovered.

According to a preferred embodiment of the present invention the inventive pharmaceutical compositions contain as active ingredient a mixture of an extract recovered with an aqueous extraction medium and an extract recovered by extracting with a not aqueous extracting medium. It is specially advantageous to use as active ingredient of the inventive pharmaceutical preparations a mixture of a major part by weight of the extract recovered with the aqueous extraction medium and a minor part by weight of the extract recovered with the not aqueous extraction medium, preferably a mixture of 10–30 parts by weight, referred to the dry weight, of the extract recovered with the aqueous extraction medium and one part by weight, referred to the dry weight, of the extract recovered with the not aqueous extraction medium. For example the extract can comprise 20 parts by weight, referred to the dry weight, of the extract recovered with the aqueous extraction medium and 1 part by weight, referred to the dry weight, of the extract recovered with the not aqueous extraction medium.

For the preparation of the active ingredients of the inventive pharmaceutical preparations preferably freshly harvested pollen of plants or predried pollen of plants are first treated with the aqueous extraction medium at a temperature of 28° C.–35° C., preferably 30°–32° C., for about 36–60 hours. Usually said extraction with the aqueous extraction medium is performed using per kg of pollen about 4–6 kg of the aqueous extraction medium.

A preferred aqueous extraction medium is a mixture of a major part, referred to the weight, of water with a minor part, referred to the weight, of an organic solvent which is water miscible, preferably miscible in any weight ratios with water. Examples for such water miscible organic solvents are lower aliphatic alcohols and lower ketones like for instance ethanol or acetone. The aqueous extraction medium preferably contains 2–30% by weight of the water miscible organic solvent and the remainder to totally 100% by weight consists of water, preferably distilled water.

An example for a suitable aqueous extraction medium is an aqueous solution containing 20% by weight of ethanol or an aqueous solution containing 5% by weight of acetone.

After said preextraction treatment with the aqueous extraction medium the pollen of plants are stirred in said aqueous extracting medium and a microorganism which metabolizes the high molecular proteins of the hull of the pollen is added. The agitation is continued maintaining the temperature in the range of 15°–35° C. for further 36–60 hours. During said period the added microorganism fermentates the outer hulls of the pollen. The microorganisms metabolize the high molecular proteins of the pollen yielding proteins of low molecular weight or free amino acids.

As already stated before, the constituents of the pollen which possibly act as allergens are high molecular proteins. Said high molecular proteins are metabolized by the microorganisms either completely or at least to such a degree, that the product recovered after said fermentation has no allergic activity at all, i.e. until the product in question contains not more than 5% by weight of proteins having a high molecular weight, referred to the dry weight of the pollen constituents.

The microorganisms used for performing said fermentation are preferably fungi. It is preferred to use for said fermentation fungi of the family of Mucor. Specific examples of fungi of the class of Mucor which can be advantageously used for degradating the high molecular proteins are: *Mucor glomerata; Mucor luteus; Mucor mucedo; Mucor flavus, Mucor corticolus, Mucor brunneus, Mucor hiemalis* or *Mucor alpinus*.

After said fermentation step the aqueous extraction medium is separated from the residues of pollen, for example by performing a filtration. The filtrate is a clear solution. Said solution contains several constituents like e.g. vitamines, several different kinds of sugars, desoxyriboside, proteins of low molecular weight, amino acids and traces of mineral constituents.

The residue of pollen, e.g. the filtre cake recovered after the filtration, is then mixed with the not aqueous organic extraction medium and further extracted. Usually said second extraction procedure is performed for about 36–60 hours, preferably at a temperature near to room temperature.

For performing said second extraction procedure usually 3–6 kg of the organic not aqueous extraction medium are used for one kg of pollen introduced into the first extracting procedure.

The preferred not aqueous organic extraction medium are water soluble or water insoluble organic solvents like lower ketones, carboxylic acid esters, dialkylethers or aliphatic or cycloaliphatic hydrocarbons. Examples for such solvents are acetone, diethylether, low boiling petroleum fractions, preferably petroleum ether or heptane.

After the pollen had been submitted to the extraction with said not aqueous organic extraction medium the remaining residues of the pollen are removed from the extraction medium, for example by filtrating or by centrifuging. The so recovered extract is a clear solutoin which contains the lipid soluble ingredients of the pollen of the plants, like e.g. steroles, waxes, chlorophylls and similar materials.

According to the inventive process there are preferably evaporated the solvents from the extract recovered with the aqueous extraction medium and from the extract recovered with the not aqueous extraction medium. The evaporation can be performed under reduced pressure and the extracts are concentrated to yield corresponding higher concentrated extracts or dry residues respectively. Said higher concentrated extracts and dry products are used as active ingredients of the inventive pharmaceutical preparations.

It is furthermore possible to prepare extracts from specific mixtures of pollen in order to provide such pharmaceutical preparations which are specially suited for the prophylactic treatment of specific allergies.

Human beings which show allergic reactions if they are contacted with pollen of plants very often show the allergic reaction if they are contacted with pollen of such plants, the pollination thereof is not performed by insects but by the wind. It is obvious that plants which are pollinated by a stream of air have to produce specially high quantities of pollen in order to secure the fertilization. It furthermore is well known that from the plants which are pollinated by the wind those are most likely to provoke an allergic reaction which have specially small sized pollen. Examples for pollen which frequently act as allergens are the pollen of the hazelbush, of the birch-tree, of the alder-tree, of the ash-tree, of the Spanish chestnut, of different grasses and of plantain, i.e. plants with the Latin name Plantago. Several persons show allergic reactions for several different kinds of pollen, however, many persons react allergically only for a certain kind of plant pollen.

When the inventive pharmaceutical preparations are prepared, it is possible to select the pollen of the starting material so that the corresponding pharmaceutical preparations have a specially high prophylactic activity for the treatment of specific allergies.

Preferred inventive pharmaceutical preparations which are administered orally are such preparations which comprise per dosage-unit, for example per tablet or per capsule 50–70 mg dry weight, for example 60 mg dry weight, of the extract of pollen recovered with the aqueous extraction medium and, furthermore, 2–4 mg dry weight, for instance 3 mg dry weight, of the extract of pollen recovered with the not aqueous extraction medium.

Processes for the preparation of the inventive pharmaceutical preparation and test results of a prophylactic treatment of persons suffering from allergies with the inventive product are further illustrated with the following examples. Said examples, however, have not to be considered to be limitative to the scope of the invention.

EXAMPLE 1

120 kg of a pollen of rye having the Latin name Secale cereale are treated with 600 kg of an aqueous solution containing 20 vol.-% of ethanol in distilled water. The pollen were stirred in said solution for 48 hours at a temperature of 30°–32° C. After said pretreatment the microorganism Mucor alpinus was added and the stirring continued at a temperature of 30° C. for further 20–30 hours.

Thereafter the aqueous medium is filtered off. Said filtrate is a clear solution and the solvent of said solution was evaporated under vacuum. The dry residue remaining after said evaporation is a product which is an active ingredient of an inventive pharmaceutical preparation.

The pollen residues which remained after the aqueous extraction medium had been filtered off, was mixed with 400 kg of acetone and stirred in this medium at room temperature for further 48 hours. After said extraction with the not aqueous extraction medium the pollen were centrifuged and the supernatant liquid was a clear solution. From said clear solution the solvent was evaporated under vacuum and the resulting dry residue is a product which can be used as active ingredient of inventive pharmaceutical preparations.

Optionally the centrifuged pollen residue which was obtained after the supernatant acetone solution had been drawn off can be submitted to a further extraction with an aqueous extraction medium and thereafter to a further extraction with a not aqueous organic solvent in order to recover further quantities of a water soluble active ingredient respectively lipoid soluble active ingredient which can be as well used as active ingredient of inventive pharmaceutical preparations.

EXAMPLE 2

Tablets were formulated which contained per tablet 60 mg of the dry residue obtained according to example 1 using the aqueous extraction medium and furthermore 3 mg of the dry residue obtained according to example 1 using the acetone as extraction medium. Said tablets were used for a prophylactic treatment of hay fever and other allergic pollen reactions and the treated persons were grown up female and male persons as well as children. To the tested persons the tablets were administered orally in the months February until the end of April. To the children which were younger than 10 years there were administered daily three tablets (in the morning, at midday and in the evening) and to the grown up persons there were administered daily twelve tablets, i.e. four tablets in the morning and the same quantities at midday and in the evening.

All tested persons had suffered in the years before of very severe allergies which were caused by pollen. The grown up female and male persons had either suffered from very severe symptoms of hay fever, like nearly permanent sneezing irritation, segregation of high quantities of watery nasal mucous, tearing eyes, swollen face and swollen mucous membrane, or the persons in question had suffered from an asthma caused by a pollen allergy. All the tested children had suffered the years before from severe asthma which had been caused by a pollen allergy, like for example a boy of eight years who was tested. The tested children and the tested grown up female and male persons who had been submitted to the prophylactic treatment with the inventive preparation were free of any symptoms of hay fever or asthma during the spring time and during the whole summer.

What is claimed is:

1. A method of treating allergies including the steps of administering a preparation containing as active ingredient an extract of pollen which contains not more than 5% by weight, referred to the dry weight of the extract of pollen, of proteins having a high molecular weight or which is completely free of proteins having a high molecular weight.

2. A method according to claim 1 in which said preparation is administered orally.

3. A method according to claim 1 wherein the extract of pollen is an extract of pollen of the plant family of the conifers, preferably the pinaceae, the plant family of the cereals and grasses, i.e. the gramineae, preferably the class of framineae or that the extract of pollen is an extract of pollen of both of said plant families or of a mixture of pollen of at least one of said plant families with pollen of other plant families, preferably pollen of the family of the liliacea, the compositae, the rosaceae, the salicaceae, the betulaceae or the ulmaceae.

4. A method according to claim 1, wherein the extract of pollen is an extract which was recovered by an extraction performed with an aqueous extraction medium or a not aqueous extraction medium or that the extract of pollen is a mixture of an extract recovered using an aqueous extraction medium and an extract recovered using a not aqueous extraction medium.

5. A method according to claim 2, wherein the extract of pollen is an extract which was recovered by an extraction performed with an aqueous extraction medium or a not aqueous extraction medium or that the extract of pollen is a mixture of an extract recovered using an aqueous extraction medium and an extract recovered using a not aqueous extraction medium.

6. A method according to claim 3, wherein the extract of pollen is an extract which was recovered by an extraction performed with an aqueous extraction medium or a not aqueous extraction medium or that the extract of pollen is a mixture of an extract recovered using an aqueous extraction medium and an extract recovered using a not aqueous extraction medium.

7. A method as in claim 1 in which said preparation is produced by a process wherein freshly harvested or dry pollen of plants are extracted with an aqueous extraction medium and thereafter the high molecular proteins present in said aqueous extract are metabolized by microorganisms yielding proteins of low molecular weight and/or amino acids and wherein said proteins of high molecular weight are metabolized until a content of the extract of said proteins of not more than 5% by weight, referred to the dry weight of the extract of pollen is reached or until the extract is completely free of proteins having a high molecular weight and wherein the pollen are isolated from the aqueous medium and the residue of pollen is further extracted with a not aqueous medium and said second extract is as well recovered.

8. A method according to claim 7 wherein from the extract recovered with the aqueous extraction medium there is evaporated the aqueous extraction medium at least partially after said extract had been submitted to the treatment with the microorganism and the resulting concentrated extract or dried extract is used as active ingredient of the pharmaceutical preparation, and that from the extract recovered with the not aqueous extraction medium the solvent is at least partially evaporated and the resulting concentrated extract or dried extract is used as active ingredient of the pharmaceutical preparation or that a mixture of the concentrated or dried extract recovered after the extraction with the aqueous extraction medium and the concentrated or dried extract recovered after the extraction with the not aqueous extraction medium is used as active ingredient of the pharmaceutical preparation.

9. A method according to claim 7 wherein the microorganism used for the metabolization of the high molecular proteins is a fungus of the family of Mucor, preferably the microorganism Mucor glomerata; Mucor luteus; Mucor mucedo; Mucor hiemalis or Mucor alpinus.

10. A method according to claim 7, wherein the aqueous extraction medium is a mixture of water and a water soluble organic solvent, preferably a lower alcohol or a lower ketone, and that the not aqueous extraction medium is a water soluble or water insoluble organic solvent, preferably a lower ketone, a carboxylic acid ester, a dialkylether, or an aliphatic or cycloaliphatic hydrocarbon or a mixture of hydrocarbons.

11. A method according to claim 8 wherein the aqueous extraction medium is a mixture of water and a water soluble organic solvent, preferably a lower alcohol or a lower ketone, and that the not aqueous extraction medium is a water soluble or water insoluble organic solvent, preferably a lower ketone, a carboxylic acid ester, a dialkylether, or an aliphatic or cycloaliphatic hydrocarbon or a mixture of hydrocarbons.

12. A method according to claim 9 wherein the aqueous extraction medium is a mixture of water and a water soluble organic solvent, preferably a lower alcohol or a lower ketone, and that the not aqueous extraction medium is a water soluble or water insoluble organic solvent, preferably a lower ketone, a carboxylic acid ester, a dialkylether, or an aliphatic or cycloaliphatic hydrocarbon or a mixture of hydrocarbons.

13. A method according to claim 10 wherein the aqueous extraction medium is a mixture of water and ethanol or water and acetone and that the not aqueous extraction medium is acetone, diethylether, a low boiling petroleum fraction, preferably petroleum ether, or heptane.

14. A method according to claim 11 wherein the aqueous extraction medium is a mixture of water and ethanol or water and acetone and that the not aqueous extraction medium is acetone, diethylether, a low boiling petroleum fraction, preferably petroleum ether, or heptane.

15. A method according to claim 12 wherein the aqueous extraction medium is a mixture of water and ethanol or water and acetone and that the not aqueous extraction medium is acetone, diethylether, a low boiling petroleum fraction, preferably petroleum ether, or heptane.

16. A method according to claim 7 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

17. A method according to claim 8 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

18. A method according to claim 9 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

19. A method according to claim 10 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

20. A method according to claim 11 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

21. A method according to claim 12 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

22. A method according to claim 13 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

23. A method according to claim 14 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

24. A method according to claim 15 wherein as active ingredient of the pharmaceutical preparation there is used a mixture of a major part by weight of the extract recovered with the aqueous extraction medium and a minor part by weight of the extract recovered with the not aqueous extraction medium, preferably a mixture of 10-30 parts by weight, referred to the dry weight, of the extract recovered with the aqueous extraction medium and 1 part by weight, referred to the dry weight, of the extract recovered with the not aqueous extraction medium.

* * * * *